(12) United States Patent
Carr

(10) Patent No.: US 6,258,528 B1
(45) Date of Patent: Jul. 10, 2001

(54) SIGNAL AMPLIFICATION METHOD

(75) Inventor: Frank Carr, Aberdeen (GB)

(73) Assignee: Scancell Limited, Nottineham (GB)

( * ) Notice: Subject to any disclaimer, the term of this patent is extended or adjusted under 35 U.S.C. 154(b) by 0 days.

(21) Appl. No.: 09/253,849

(22) Filed: Feb. 22, 1999

Related U.S. Application Data

(63) Continuation of application No. PCT/GB97/02254, filed on Aug. 22, 1997, now abandoned.

(30) Foreign Application Priority Data

Aug. 22, 1996 (GB) .................................................. 9617631

(51) Int. Cl.⁷ ............................. C12Q 1/70; G01N 33/53; G01N 33/561; G01N 33/542
(52) U.S. Cl. ................................ 435/5; 435/7.1; 436/516; 436/536; 436/829
(58) Field of Search ......................... 435/7.9, 7.1, 7.91, 435/7.7, 7.72, 7.5, 7.6, 7.71, 14, 5; 436/516, 536, 829, 515

(56) References Cited

U.S. PATENT DOCUMENTS

| | | | |
|---|---|---|---|
| 4,483,921 | 11/1984 | Cole | 435/7 |
| 4,713,324 | 12/1987 | Fox et al. | 435/4 |
| 5,006,473 | 4/1991 | Bouma et al. | 436/516 |
| 5,196,306 | 3/1993 | Bobrow et al. | 435/7.9 |

FOREIGN PATENT DOCUMENTS

| | | |
|---|---|---|
| 0243001 | 10/1987 | (EP) . |
| 0300682 | 1/1989 | (EP) . |
| 0518319 | 12/1992 | (EP) . |
| 0556745 | 8/1993 | (EP) . |

OTHER PUBLICATIONS

Braman et al., Biotechnology, v. 2, pp. 349–355 (1984).
Freytag et al., J. Immunological Methods, v. 70, pp. 133–140 (1984).
Titball et al., FEMS Microbiology Letters, v. 110, pp. 45–50 (1993).
Yamamura Soichiro Patent Abstracts of Japan, Publ. No. 03100466; Apr. 25, 1991.

*Primary Examiner*—John S. Brusca
*Assistant Examiner*—Stephen Siu
(74) *Attorney, Agent, or Firm*—Hale and Dorr LLP

(57) ABSTRACT

The present invention relates to a method for the amplification of or creation of A signalling event for detection of a probe which reacts with a test substance, the method comprising causing the test substance to react with the probe and identifying the reaction of the test substance with the probe by release of a signalling moiety from a vesicle. The invention also relates to a kit for the detection of a probe which reacts with a test substance, the kit comprising a vesicle which contains a signalling moiety.

13 Claims, 1 Drawing Sheet

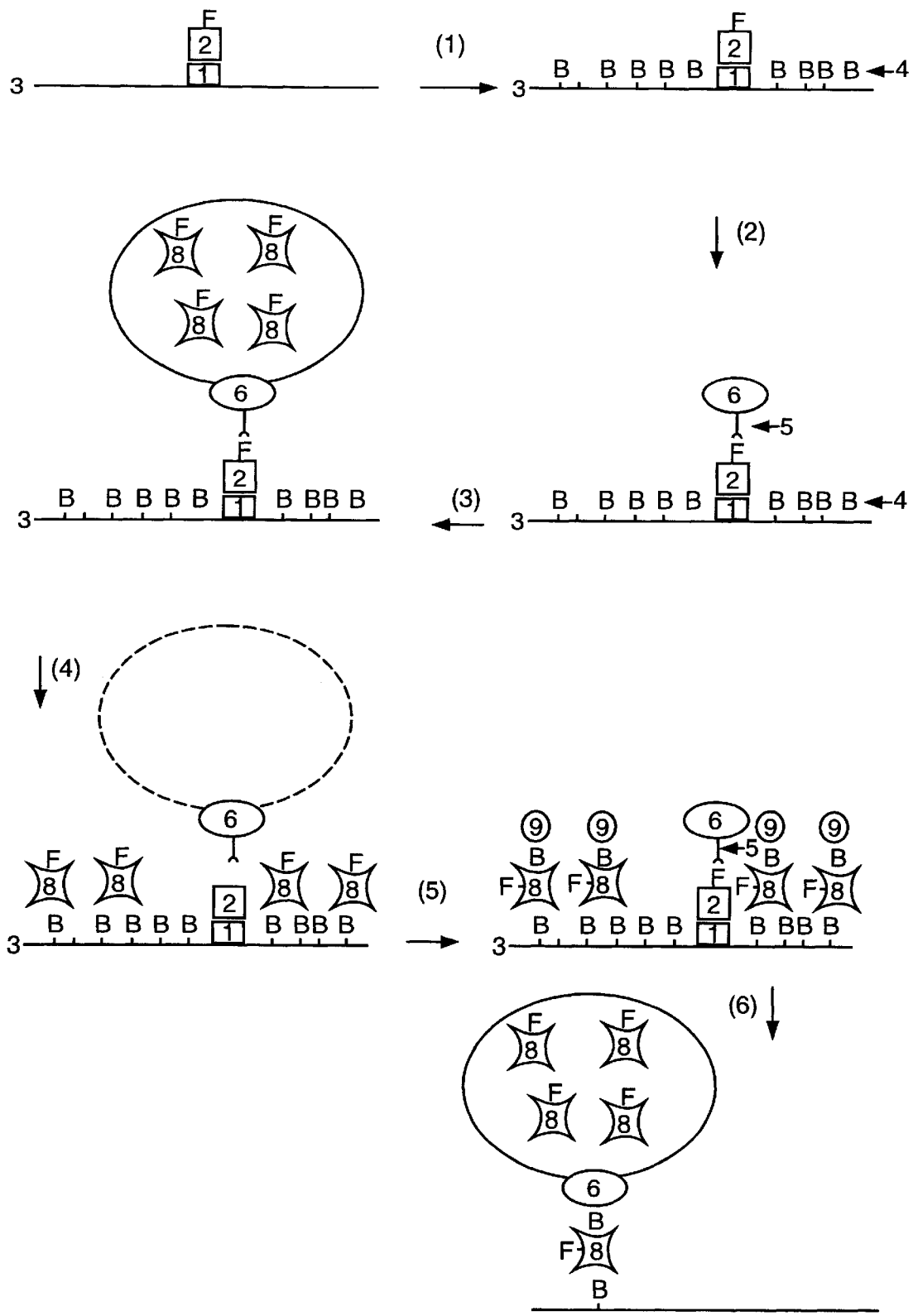

SIGNAL AMPLIFICATION METHOD

This is a continuation application of international application number PCT/GB97/02254, filed Aug. 22, 1997, abandoned, which in turn claims priority to GB 9617631.8, filed Aug. 22, 1996.

The present invention relates to a method for the amplification of or creation of a signalling event for detection of a probe which reacts with a test substance, the method comprising causing the test substance to react with the probe and identifying the reaction of the test substance with the probe by the release of a signalling moiety from a vesicle. Preferably the signalling moiety is in an active but ineffective form and/or the signalling moiety is deposited on a solid phase in the vicinity of the probe. The invention also relates to a kit for the detection of a probe which reacts with a test substance, the kit comprising a vesicle which contains a signalling moiety.

Many systems for the quantitative and qualitative analysis of target substances are known. However, the need for simpler diagnostic assays with improved sensitivity is an ongoing aim and desire in the art.

U.S. Pat. No. 5,196,306 describes a method for detection of a probe through amplifying the signal through an enzyme activation system. In this system, the enzyme which comes into contact with the probe converts an inactive substrate ("conjugate") into an activated conjugate which can then be deposited onto a solid phase or wherever a receptor for the activated conjugate is immobilised. This invention therefore provides for enzymatic generation of multiple signalling molecules for each probe although the choice of signalling molecules is limited to those generated by specific substrates which can yield a reactive product which binds to a solid phase. Potential disadvantages of U.S. Pat. No. 5,196,306 relate to the enzyme having a rate-limiting turnover of conjugate and the enzyme being subject to inhibition by the sample or by the accumulating active conjugate. In addition, specific inactive enzyme substrates are needed for conversion into activated conjugates for deposition onto a receptor thus reducing the flexibility of the invention for use in many other ligand-receptor systems. Thus, simpler amplification methods are required which do not require an enzymic conversion step to generate a reactive conjugate.

The present invention has the advantage over U.S. Pat. No. 5,196,306 that an enzyme and enzymatic substrate is not needed for direct generation of an activated signalling molecule. Indeed, in the present invention, the signalling molecule is presented in its activated form and not altered by an enzyme but rather is presented within a vesicle which is brought into the proximity of the prove by the binding molecule. This provides great flexibility in the range and types of signalling molecules which can be used in the present invention and also potentially provides more rapid reaction kinetics whereby generation of multiple signalling molecules are not directly dependant on the turnover rate of an enzyme.

Accordingly, a first aspect of the invention provides a method for the amplification and/or creation of a signalling event for the detection of a probe which reacts with a test substance, the method comprising causing the test substance to react with a probe, and identifying the reaction of the test substance and the probe by the release of a signalling moiety from a vesicle.

For the purpose of this invention, the term "probe" means a molecule or molecules with the ability to react with a test substance in such a way as to provide a means for detection or quantitation of said test substance.

Whilst the probe might be a nucleic acid probe which hybridises to a target nucleic acid or an antibody which binds to a target antigen, it will be understood by those skilled in the art that the probe could also be any molecule which constitutes one element of a binding pair whereby the probe binds to the other element of the binding pair as part of the test.

In order for the release of signalling moieties from the vesicle to indicate the presence and quantity of the target substance, either the vesicle or the element which causes release of the signalling moiety from the vesicle is preferably in close proximity to the target substance and/or the probe. This can be effected in many ways, all of which are covered by the present invention. In particular, the vesicle or the element which causes release of the signalling moiety may be brought into close proximity to the target substance and/or the probe by one or more binding molecules. "Binding molecule" means a second molecule or secondary molecules which bind(s) to the probe and/or target substance in such a way as to introduce, in close proximity to the probe and/or test substance, a source of detectable signalling moiety. Suitable binding molecules include antibodies, which may or may not be modified with further ligands (including further binding molecules), nucleic acid sequences, biotin, avidin or streptavidin, or any ligand (and may also be a binding molecule) which can be conjugated to either the test substance, the probe, or to a molecule which binds, directly or indirectly to either the test substance or the probe. The ligand may also bind to either the vesicle or the element which causes release of the signalling moiety.

The probe may be one part of a non-immune or immune pair (the test substance being the other part). Preferably the probe is a nucleic acid sequence such as DNA, or an antibody. Most preferably the probe is modified to include a ligand (also optionally a binding molecule), to which can be subsequently bound another molecule through which a signalling moiety can come into close contact with the probe and/or the test substance. The ligand may be natural or unnatural (synthetic molecule). Examples of ligands include fluorescein, a lipase, an antibody, biotin, streptavidin etc. In the context of the invention, the ligand on the probe may be either undetectable itself or, as with fluorescein, detectable in its own right. As a result of contact with the binding molecule and release of a signalling moiety from a vesicle, the probe should become respectively either detectable or should become more easily detectable as a result of introducing a stronger or more easily measurable signal. The signal may be amplified by virtue of introduction of multiple signalling molecules for each single probe.

In the method of the present invention, a probe is allowed to react with a test substance. The former, or the latter may be immobilised onto a solid phase. Where the test substance is immobilised onto a solid support, excess probe can be washed away from the reaction before further steps in the method are carried out.

The method can follow by the addition of a molecule (may be considered as a binding molecule) which comprises an element which binds and/or reacts in some way with the probe and/or with a ligand on the probe. The binding molecule may comprise either i) an element which either directly or indirectly can causes release of a signalling molecule from a vesicle, or ii) a vesicle which comprises a signalling moiety. The binding molecule which comprises either of components i) or ii) above need not bind directly to the probe or to the test substance. It may bind indirectly, i.e. via other binding molecules, as long as the ultimate aim of bringing the vesicle into close proximity to the probe and/ or test substance is obtained.

The next step in the method is to cause the release of a signalling moiety from the vesicle. This step is preferably sequential to the previous step. However, it may be that the probe already had bound to it a molecule which either comprised a vesicle which comprises a signalling moiety or an element which directly causes release of a signalling moiety from a vesicle. Preferably, the vesicle comprises more than one signalling moiety which may be the same or different types of molecules. Where the probe/test substance reaction, after addition of one or more binding molecules, comprises a vesicle which contains the signalling moiety, it is usually necessary to add to the system an element which causes release of the signalling moiety from the vesicle. The selection of such elements will depend on the composition of the vesicle. The element can cause release of the signalling moiety by any means. A simple and suitable means according to the invention is an element which breaks open the wall of the vesicle thus releasing the signalling moiety.

On the other hand, where the probe/test substance reaction, after addition of one or more binding molecules comprises an element which causes release of the signalling moiety from the vesicle, then it is usually necessary to add to the system a vesicle which comprises a signalling moiety.

In all of the above scenarios, the release of the signalling moiety occurs in close proximity to the probe/test substance reaction.

The method according to the invention can be performed where the target molecule initially is either in solution or bound to a solid, or semi-solid phase. Preferably, after release from the vesicle, the signalling moiety is deposited on a solid phase in the vicinity of the probe.

Preferably the signalling moiety which is released from the vesicle reacts and/or binds with said solid and/or semi-solid phase. Molecules may, but need not be necessarily be introduced onto the solid phase in order to operate this feature of the invention. Existing molecules which are present on the solid phase or even on the probe, test substance or one or more added binding molecules can be used for binding/reacting with the signalling moiety released from the vesicles.

The result of performing the test in the preferred modes is that the signalling moiety is deposited (and optionally reacts) with a solid phase to provide a signal or to amplify a signal. Furthermore, it is possible to use this deposited (and optionally bound) signalling moiety to achieve further rounds of amplification. This can be achieved, for example, where the signalling moiety comprises a component (e.g. ligand) to which a binding molecule can associate which is conjugated directly or indirectly with a lipase. By addition of further vesicles an additional release of signalling moiety can be achieved. By providing a signalling moiety with such a ligand, multiple rounds of signal amplification can therefore be achieved through cycles of vesicle degradation, signal deposition and binding to a ligand of the deposited signalling moiety. In a preferred embodiment, whereby the vesicle is loaded with streptavidin which can react with biotin molecules immobilised onto the solid phase, the immobilised streptavidin can have spare binding sites for additional binding molecule such as a biotinylated antibody to which a lipase can be attached either directly or indirectly. The lipase is then able to cause amplification of the original signal by release of further signalling moiety from further vesicles (which, in this case release the signal upon contact with the lipase).

Most preferably, the signalling moiety which is released from the vesicle, reacts with a receptor on one or more solid phases, as described above. The signalling moiety thus coats the solid phase in the vicinity of the probe, resulting in an area of enhanced signal in the vicinity of the probe. The receptor is any molecule with the ability to bind and/or react with one or more of the signalling moieties from the vesicle. As described above, a preferred feature of the invention is that the signalling moieties which have reacted with receptors on a solid phase can be used to further amplify the signal for the probe/test substance reaction. This amplification step can be one or more of a variety of amplification steps, depending on the signalling moiety. All that is required for further amplification steps is that the signalling moiety comprises either: i) an element which causes a further signal in the vicinity of the probe or ii) a portion which binds, directly or indirectly to an element which causes a further signal in the vicinity of the probe. These elements may require further components in the system to cause the release of the further signal.

A preferred feature of the invention is that the signalling moiety is provided in the vesicle in an active, but ineffective form. This includes the quenching of a signal by the vesicle and preferably, the fact that the signalling moiety reacts with a receptor to cause the signal to be identified. Other examples of active but ineffective signalling moieties include an enzyme which are ineffective because of a lack of substrate or a substrate which is ineffective because of a lack of enzyme. Examples of signalling moieties include, but are not limited to those which comprise fluorogenic, chromogenic, electrochemical or chemiluminescent molecules, radioactive isotopes, or two or more thereof. Specific examples include $^{125}$I, fluorogenic molecules such as fluorescein, rhodamine and green fluorescent protein, chromogens such as orthonitrophenyl-B-L-pyronidyl, b-napthalamide-B-L-pyronidyl, and similar substrates. Certain molecules may be detected electrochemically or optically using electrical or optical sensors. For example, biotinylated horseradish peroxidase may be released from the vesicle and bind to the surface of a silicon chip via a streptavidin layer. Hydrogen peroxide is then added in order to generate an electron which can be detected via the chip. Similarly, optical signals such as fluorescence may be detected in the vicinity of a solid phase via an electronic sensor. Similarly, the deposition of molecules on a solid phase may be detected by sensor which measures surface plasmon reasonance such as the Biacore sensor available from Pharmacia.

Preferred signalling moieties of the present invention include a component which reacts with a receptor molecule (may be present on a solid phase). These components may be necessary if the signal is to be produced as a result of deposition (and or binding) on a solid or semi-solid surface. Such components include a binding protein, a bacterophage, a virus, a nucleic acid sequence an enzyme or a combination of two or more thereof. The nucleic acid sequence may be a primer suitable for PCR, in which case two nucleic acid sequence primers are preferred. These components which react with a receptor may be bound to one or more other components, such as one or more signalling moiety.

The vesicle according to the present invention may be any signalling moiety-carrying container which can be caused to release the signalling moiety. Usually, the vesicle surrounds the signalling moieties, but this is not mandatory. The signalling moiety can be incorporated in any manner (eg embedment) in the vesicle which requires release of the signalling moiety therefrom in order to obtain a signal in accordance with the invention. Suitable vesicles of the invention, which are in no way limiting include: red blood cells, any other eukaryotic cell, a prokaryotic cell, liposomes, a lipid-based emulsion, or a lipid-based artificial membrane. Any vesicle can be used where a means for release of the signalling moiety is identified. Biological cells, such as those described above may be accessed by the action of a lipase on the cytoplasmic membrane. Lipases or other enzymes may also be used which disrupt cell membranes e.g. the enzyme beta-galactosidase when membranes are constituted to include the ganglioside GMI (EP-A-0300682) or other lipopolysaccharides which can be digested by enzymes in such a way to destroy a vesicle, such as a liposome. The vesicle may incorporate one or more other molecules in addition to the signalling moiety.

Elements (means) which cause release of the signalling moiety from the vesicle require selection according to the nature (and also possibly the content) of the vesicle. It will be additionally understood that whilst the element which can cause release of the signalling moiety from a liposome is preferably a lipase, this element could be any other element which can achieve the same result, such as a detergent, animal complement (e.g. Braman et al., Biotechnology vol. 2 (1984) p349–355) and cytolysin (e.g. Freytag et al., J. Immunological Methods vol. 70 (1984) p133–140).

The element causing release of the signalling moiety may be provided in 2 inactive subunits, both of which may be required to cause release of molecules from the vesicle. For example, it has been shown that lipases such as bacterial phospholipase C can be provided in 2 inactive subunits which can pair together to reconstitute enzyme activity (Titball et al., FEMS Microbiology Letters vol. 110 (1993) p45–50). Thus, one subunit can be provided which is attached to a probe or a molecule which binds to a probe, while the other is provided on another probe, or even provided on the vesicles themselves in such ways as to reconstitute lipase activity leading to release of the signalling moiety from the vesicle. Where the reconstitution of means causing "release from the vesicle" activity is dependant on 2 subunits, the test system can be configured such that reconstituted activity of the element which causes release of the signalling moiety from the vesicle is dependant on the interaction of 2 probes with a test substance (target) or the prevention of interaction by the test substance. Such cases are examples of homogeneous tests where the signalling moiety is simply released into solution from the vesicles as the read-out in the test.

As a further embodiment to this vesicle-degrading element, the element could instead be a member of a different binding pair whereby the other element of the binding pair is embedded in the vesicle such that the vesicle can become associated with the probe and the solid phase. In this alternative, vesicles attached would subsequently be degraded by addition of a suitable agent such as a lipase or a detergent which would then effect the release of the signalling moiety.

Usually, the release of the signalling moiety from the vesicle is by degradation or breaking of the vesicle wall (usually chemical), although other methods are also within the scope of the present invention such as piercing the vesicle cell wall with a perforin or other membrane channel, by complement fixation or by detergent lysis.

According to a second aspect of the invention, there is provided a kit for the detection of a probe which reacts with a test substance, the kit comprising a vesicle which contains a signalling moiety. The kit may comprise a package and/or instructions as to the use of the kit.

The kit may further comprise one or more of the following components:

i) a probe,
ii) means to release the signalling moiety from the vesicle,
iii) one or more other moieties for the signalling moiety to react with.

In iii) above, the reaction of the signalling moiety may produce a signal, or amplify a signal or may require a further component or binding molecule to produce a signal, or further amplify a signal.

All of the features of the first aspect of the invention described above also apply to the second aspect. Further, the preferred features of the first aspect are also preferred for the second aspect.

The kit according to the second aspect can be formulated and presented as other kits known in the art. In many cases, the test substance to identified will be readily characterised and thus the kit will also supply a probe for the test substance which will provide suitable binding with the test substance to be identified and/or quantified.

All of the essential and optional components of the first and second aspects of the invention are known in the art and can be prepared according to methods and techniques which are standard and known in the art. For example, vesicles according to the invention can be prepared as described in any one of the examples described herein.

In one preferred embodiment of the present invention, the probe is a nucleic acid probe which is conjugated to the ligand fluorescein. The binding molecule is anti-fluorescein. To the anti-fluorescein antibody is either conjugated directly a lipase (especially a phospholipase) or the lipase is added indirectly via a lipase-conjugated second antibody which binds to the anti-fluorescein. The vesicle which contains the signalling moiety is then added and comes into contact with the lipase which causes the vesicle to be degraded to release the contents of the vesicle in the vicinity of the probe. If a receptor is present on or has been reacted with the solid phase, then the signalling moiety will bind to the receptor and thus coat the solid phase in the vicinity of the original probe. In the preferred embodiment, the receptor is biotin and is added after the probe in the form of a biotin conjugate with an active group which reacts with the solid phase (and can also react with structures in the test substance and the probe).

In an alternative, embodiment, the vesicle is a liposome and the liposome is loaded with fluorescein-labelled streptavidin. Upon contact of the fluoresceinated probe with the sample, the lipase-conjugated anti-fluorescein antibody binds to the probe and the lipase of the conjugate causes local degradation of added fluoresceinated streptavidin-loaded liposomes. The fluoresceinated streptavidin is released locally and combines with the biotin molecules which coat the solid phase. An area of enhanced fluorescence is produced in the vicinity of the probe In another preferred embodiment of the present invention, the probe is an antibody, which has conjugated to it the ligand biotin and the binding molecule is lipase-conjugated anti-biotin or lipase-streptavidin. Preferably, the liposome is then loaded with anti-biotin or streptavidin conjugated to horseradish peroxidase (HRP) or alkaline phosphatase (AP) and this can react with biotin molecules immobilised onto the solid phase. If required, additional biotinylated HRP or AP can then be added to further amplify the signal by virtue of free biotin receptors on the enzyme-streptavidin molecules.

Included in the present invention is the use of vesicles (eg liposomal vesicles) containing two or more signalling species. Also included in the present invention is the use of a signal amplification system exploiting two or more different vesicles, each of which may be charged with different signalling/reporter species. It will be obvious to those skilled in the art that vesicles such as liposomal vesicles may be formulated to carry almost any number of different molecular species and that their membranes may be manipulated to show differential susceptibility to disruption by a number of different enzymatic and other lipoactive agents. In the preferred embodiment liposomes are formulated to be sensitive to disruption by phospholipase C and derivatives thereof. In a preferred embodiment liposomes contain avidin-FITC and deliver a green fluorescent signal. In further embodiments, liposomes containing avidin-rhodamine are made such that on disruption, a red fluorescent signal is delivered. Also, liposomes containing a mixture of avidin-rhodamine and avidin-FITC may also be made which upon disruption deliver a yellow signal. Liposomes prepared with saturated lecithin/cholesterol membranes or sphingomyelin/cholesterol membranes show little or no disruption with phospholipase C but remain susceptible to disruption to other lipoactive agents such a complement. Liposomes prepared containing monosialogangliocide (GM1) or other gangliocides are susceptible to degradation by the enzyme β-galactosidase or derivatives thereof. β-galactosidase has no effect on liposomes prepared with standard lecithin/cholesterol mixtures or any other non-syalic components.

With such a multiplicity of possible vesicle compositions and reporter/signalling species, it is clearly possible to produce a system where the simultaneous detection of two or more different targets each distinguishable from the other by virtue of a different reporter is able to work. The ability to multiplex reactions and simultaneously assay several targets in a single amplification step is of particular importance in settings where clinical materials may be limiting and rapid testing of the essence. In particular this will include applications such as antenatal testing by fluorescence in situ hybridisation and other similarly important clinical applications.

The invention is illustrated by the FIGURE which shows the overall scheme of the basic invention (steps 1 to 4) as applied to a typical assay with a DNA probe molecule 2 with an optional round of amplification (steps 5 and 6). This FIGURE illustrates an example where the DNA probe 2 hybridises to the target nucleic acid 1 on the solid phase 3 and the hybridised solid phase is reacted with a reactive biotin conjugate (step 1) thus coating the solid phase with biotin conjugate (4). In step 2, an anti-fluorescein antibody 5 conjugated to a phospholipase 6 binds to the hybridised DNA probe 2. In step 3, the liposome 7 containing encapsulated fluoresceinated-streptavidin 8 is added thus causing degradation of the liposome. In step 4, the fluoresceinated-streptavidin 8 is released and binds to the biotin groups 4 on the solid phase thus resulting in fluorescence associated with the solid phase. In step 5, biotinylated-phospholipase conjugate 9 is added and binds to the free biotin sites on the immobilised fluoresceinated-streptavidin 8. In step 6, further lipsome 7 containing encapsulated fluoresceinated-streptavidin 8 is added thus causing further degraded liposomes leading to additional deposits of fluoresceinated-streptavidin on the solid phase.

The following examples serves to illustrate the invention but should not be regarded as limiting the scope of the invention for which there are a large number of operational variations all of which fall within the scope of the invention.

EXAMPLE 1

Fluorescence in situ Hybridisation (FISH)

A fluorescence in situ hybridisation (FISH) assay for the human chromosome 18 from normal male peripheral blood lymphocytes was carried out using the manufacturer's recommended protocol and a human chromosome 18 FITC-labelled interphase probe (Biovation, Aberdeen, U.K; #18C010.1x). Using the standard protocol as a control, chromosomes and nuclei were counterstained using a DAPI/antifade solution (Biovation, Aberdeen, UK; #ANC002), and visualised using a fluorescence microscope fitted with a filter to facilitate simultaneous viewing of fluorescein and DAPI signals.

For the signal amplification protocol, following the hybridisation and washing steps, biotinylation of the sample glass microscopy slides used the biotinylating agent EZ-link Sulfor-NHS-LC-Biotin (Pierce, Chester, U.K.; #21335). The reagent was dissolved in dimethylformamide (Sigma, Poole, U.K.; #27054-7) at a concentration of 100 mg/ml. The biotinylation reaction was carried out by incubation of the slide with the biotinylation reagent for 30 minutes at room temperature in the dark, followed by 3 successive 2 minute washes in ice cold phosphate buffered saline. In different experiments, biotinylation was performed on prepared slides either before fluorescence in situ hybridisation (FISH) or after the FISH procedure.

Conjugation of anti-fluorescein monoclonal antibody (Boehringer, Lewes U.K., #1426320) to phospholipase C (Sigma, Poole, U.K., #P4039) used using Sulpho-MBS (m-Maleimidobenzoyl-N-hydroxysuccinimide ester) (Pierce, Chester, U.K., #22312) as cross-linking reagent. Conjugation was achieved using the manufacturer's recommendation protocol. Reagents were desalted and purified post-conjugation using a G25 Sephadex column (Pharmacia, Uppsala Sweden; #17-0851-01), and conjugation verified by SDS polyacrylamide gel electrophroresis and Coomasie Blue staining according to standard protocols.

Liposomal vesicles containing streptavidin-fluorescein were produced by mixing the lipids L-phosphatidylcholine and oleoyl-palmitoyl cholesterol. Streptavidin-fluorescein (Boehringer, Lewes, U.K.; #1055097) at a concentration of 100 mM in 10 mM Tris pH8.0 was added to 10 mg of a mixture of 1.5:1 L-alpha-phophatidylcholine and cholesterol (Sigma Poole U.K.; #13906). Vesicles were formed following repeated cycles of vigorous mixing and allowing the solution to stand at room temperature. The volume of the liposomal solution was increased by addition of 10 mM Tris 10 mM pH8.0 and liposomes purified from unincorporated components by gel filtration through a G25 Sephadex column (Pharmacia, Uppsala Sweden; #17-0851-01) with borate buffered saline (BBS; 0.2M sodium metaborate, 7.5 g/l NaCl, 1.8g/l $CaCl_2.2H_2O$, pH adjusted to 7.0 with boric acid). Integrity of the eluted liposomes was assessed by microscopy where intact liposomes were compared to control preparations lysed by treatment with a solution of 1% (v/v) NP-40 (Pierce, Chester, U.K.; #28324). Liposomes were diluted in BBS to give a final 10 mM streptavidin-fluorescein and 100 ul was added to the hybridised slides and incubated for various times at 37° C. Slides were subsequently washed for 3×5 minutes in a solution of 2×SSC (1×SSC is 0.15M NaCl/0.015M Na Citrate pH7.0). Slides were rinsed in water, and counterstained and mounted for fluorescence microscopy using a DAPI-antifade solution (Biovation, Aberdeen, U.K. #ANC002). Comparison of fluorescent signals after the phospholipase amplification method compared to signals from the method using direct FITC-labelled probe alone resulted in an estimated 10-fold increase in fluorescence signal after 10 minutes after incubation with liposomes rising to a 50-fold increase after 1 hour incubation.

EXAMPLE 2

Fluorescence in situ Hybridisation (FISH)

Method for Fluorescence in situ Hybridisation (FISH)

A fluorescence in situ hybridisation (FISH) assay for the human chromosome 18 from normal male peripheral blood lymphocytes was carried out using a human chromosome 18 FITC-labelled probe (Biovation, Aberdeen, U.K.; #FPF1810.5x ). A number of test slides were prepared using normal male peripheral blood lymphocytes which had been cultured for 3 days and treated with colcemid (Life Technologies, Paisley UK) to arrest mitosis according to standard protocols. Fixed cells were applied to glass microscopy slides and checked for the presence of mitotic figures by light microscopy before proceeding with the fluorescence in situ hybridisation (FISH) assay. Slides were stored in 70% ethanol at −20° C. until required for assay. Slides were equilibrated to room temperature before washing in a solution of 2×SSC (1×SSC is 0.15M NaCl/0.015M Na Citrate pH7) at room temperature for 5 minutes. Slides were dehydrated by successive 2 minute incubations in 70%, 85% and 100% ethanol at room temperature.

The chromosome 18 FITC-labelled probe solution and all equipment were pre-warmed to 37° C. before use. 10 $\mu$l of probe was added to an area of the microscope slide and covered with a glass coverslip. The probe and target DNA in the sample, were denatured by placing the slide on to a hotplate for 5 minutes at 75° C. The slides were placed in the dark at 37° C. and hybridisation allowed to proceed for at least 8 hours.

Following hybridisation, the coverslips were removed from the slides and the slides washed using three successive 5 minute incubations in a solution of 50% formamide/1× SSC pH7 at 45° C.; one 5 minute incubation in a solution of 1×SSC pH7 at 45° C., and one 5 minute incubation in a solution of 4×SSC 0.05% v/v/Tween 20 at room temperature. Slides were either mounted for counterstaining and examination by fluorescent microscopy, or incubated with other components of the signal amplification method. Counterstaining for microscopy was achieved by applying 10 $\mu$l DAPI-antifade solution (Biovation ltd Aberdeen # ANC002) to the slide and covering the area with a coverslip. Slides were incubated in the dark for 10 minutes before examination.

Method for Forming Biotin Layer on Test Slides for Signal Amplification

For the signal amplification protocol, following the hybridisation and washing steps, biotinylation of the sample glass microscopy slides was achieved using the biotinylating agent EZ-link Sulfor-NHS-LC-Biotin (Pierce, Chester, U.K.; #21335). The reagent was dissolved in dimethylformamide (Sigma, Poole, U.K; #27054-7) at a concentration of 10 mg/ml. The biotinylation reaction was carried out by incubation of the slide with the biotinylation reagent for 30 minutes at room temperature in the dark, followed by three successive 2 minute washes in ice cold phosphate buffered saline. In different experiments, biotinylation was performed on prepared slides either before fluorescence in situ hybridisation (FISH) or after the FISH procedure.

Method for Conjugation of PLC to Targeting Antibody

Conjugation of anti-fluorescein monoclonal antibody (Boehringer, Lewes U.K.; #1426320) to phospholipase C (Sigma, Poole, U.K.; #P4039) was carried out using Sulpho-MBS (m-Maleimidobenzoyl-N-hydroxysuccinimide ester) (Pierce,Chester, U.K.; #22312) as cross-linking reagent. Conjugation was performed using the manufacturers recommended protocol. Reagents were desalted and purified post-conjugation using G25 Sephadex columns (Pharmacia, Uppsala Sweden; #17-0851-01), and conjugation verified by SDS polyacrylamide gel electrophroresis and Coomasie Blue staining according to standard protocols (in *Antibodies A Laboratory Manual* eds Harlow E. & Lane D. Cold Spring Harbour Laboratory Press 1988, NY, U.S.A.).

In a preferred embodiment, this invention exploits bacterial phospholipase C which has been chemically conjugated to a targeting antibody. The use of recombinant forms of this enzyme and any other lipoactive moieties which have been engineered to show bifunctional activity, for example by recombinant linkage with an antibody variable region or derivative binding determinant from an antibody, is also included within the scope of the present invention.

Method for Expression of a Recombinant PLC Single Chain Antibody Molecule

Small scale expression of a recombinant PLC single chain antibody was achieved using a bacterial plasmid expression vector inducible by IPTG. A cell pellet from a 5 ml overnight culture was re-suspended in 7.5 LB culture medium containing 50 $\mu$g/ml ampicillin. Following a one hour incubation at 37° C., IPTG was added to the culture to a concentration of 0.1 mM and the culture further incubated at 25° C. for 3 hours. Cells were collected by centrifugation and gently re-suspended in 1 ml of ice cold 30 mM Tris/HCl/ 20% sucrose pH 8.0. Cells were incubated on ice for 10 minutes and recovered by centrifugation in a microcentrifuge for 1 minute. The supernatant was collected for analysis by ELISA, and the cells re-suspended in 1 ml ice cold 5 mM $MgSO_4$. Following incubation in ice for 10 minutes, the cells were again collected by centrifugation. The cell pellet was re-suspended in 0.5 ml PBS and the cells fractured by repeated cycles of freeze-thaw. The supernatant from the freeze-thaw process was collected and used in ELISA and functional assays without further purification. For some experiments recombinant molecules were purified from the supernatant using commercially supplied affinity purification columns designed for single step purification of histidine tagged fusion proteins and protocols provided by the supplier (Pharmacia Uppsala, Sweden). The presence of recombinant PLC fusion protein was assessed by ELISA, using a goat anti-human kappa HRP conjugate (NA933 Amersham UK).

Method for Producing Liposomal Vesicles Containing Streptavidin-Fluorescein

Liposomal vesicles containing streptavidin-fluorescein were produced by mixing the lipids L-phosphatidylcholine and oleoyl-palmitoyl cholesterol. Streptavidin-fluorescein (Boehringer, Lewes, U.K.; # 1055097) at a concentration of 100 mM in 10 mM Tris pH8.0 was added to 10 mg of a mixture of 1.5:1 L-alpha-phophatidylcholine and cholesterol (Sigma Poole U.K; #13906). Vesicles were formed following repeated cycles of vigorous mixing and allowing the solution to stand at room temperature. The volume of the liposomal solution was increased by addition of 10 mM Tris 10 mM pH8.0 and liposomes purified from unincorporated components by gel filtration through a G25 Sephadex column (Pharmacia, Uppsala Sweden; #17-0851-01) with borate buffered saline (BBS; 0.2M sodium metaborate, 7.5 g/l NaCl, 1.8 g/l $CaCl_2.2H_2O$, pH adjusted to 7.0 with boric acid). Integrity of the eluted liposomes was assessed by microscopy where intact liposomes were compared to control preparations lysed by treatment with a solution of 1% (v/v) NP-40 (Pierce, Chester, U.K.; #28324). Liposomes were diluted in BBS to give a final 10 mM streptavidin-fluorescein.

Method for Producing Unilamellar Liposomes of Varing Composition and Containing Avidin-Fluorescein Cholesterol, phosphatidyl serine (PS) and grade 1 egg yolk lecithin were obtained from Lipid Products Ltd (Nutfield UK). Lipids were supplied dissolved in chloroform methanol. Cholesterol was supplied in powder form. Mixtures of the components were made at varying molar ratios (e.g. 7:7:1 egg yolk lecithin:PS:cholesterol) into 100 ml florentine flasks. At all stages were practicable, flasks and solutions containing lipid mixtures were gassed with $N_2$ to reduce lipid oxidation. The lipid mixture was dried to a film using a rotary evaporation system (R-3000 Buchi Switzerland), solvent was evaporated at 60° C. Following drying, 0.5 mg (0.5 ml) of avidin-fluorescein solution (A3101, Vector Labs, Peterborough UK) was added to the flask, and lipids allowed to hydrate for 2 hours at room temperature. During this incubation flasks were mixed intermittently by vortex mixer. Following re-hydration, the liposomal suspension was extruded to produce unilamellar liposomes using a Lipofast Basic extruder (LF-1, Glen Creston Ltd, Stanmore UK) fitted with 200 nm pore size membranes. In some experiments 50 nm pore size membranes were used. In all cases extrusion was carried out for a minimum of 20 cycles. Lipid preparations were assessed for avidin-fluorescein loading by heating to >65° C. at which point the white milky suspension changed colour to green as the liposomes underwent thermal lysis to release the green avidin-fluorescein. Liposomes were stored in $N_2$ gassed vials at 4° C.

Method for Applying Liposomes to Biotinylated Target Slides

Hybridised and biotinylated slides were incubated with 100 µl PLC anti-fluorescein conjugate at approximately 50 µg/ml in a solution of phosphate buffered saline (PBS) 5% (w/v) bovine serum albumin (BSA) (Sigma, #A7906, Poole, UK). A coverslip was applied to the area of the solution and incubation was carried out for 20 minutes at 37° C. Slides were washed three times in a solution of 2×SSC (1×SSC is 0.15M NaCl/0.015M Na Citrate pH7.0) for 5 minutes each time at room temperature. 100 ul prepared liposome suspension was added to the washed slide and incubated for various times at 37° C. in the dark. Slides were subsequently washed for 3×5 minutes in a solution of 2×SSC. Slides were rinsed in water, counterstained and mounted for fluorescence microscopy using a DAPI-antifade solution (Biovation, Aberdeen, U.K.#ANC002). Comparison of fluorescent signals after the phospholipase amplification method compared to signals from the method using direct FITC-labelled probe alone resulted in an estimated 10-fold increase in fluorescence signal after 10 minutes after incubation with liposomes rising to a 50-fold increase after 1 hour incubation.

EXAMPLE 3

Fluorescence in situ Hybridisation (FISH) With Two-Layer Signal Enhancement

Fluorescence in situ hybridisation (FISH) to preparations of human peripheral blood lymphocytes was performed using an FITC labelled probe for chromosome 18 (Biovation #FPF1810.5x Aberdeen, UK). Sample preparation, hybridisation conditions and post hybridisation washes were carried out as described for Example 2. Following post-hybridisation washes, slides were further reacted with the biotinylating agent EZ-link Sulfor-NHS-LC-Biotin (Pierce, Chester, U.K.; #21335) as described previously. Unilammellar liposomes containing avidin-FITC were prepared as described previously. PLC-anti-fluorescein conjugates were also prepared as described in Example 2.

A first round of amplification was performed essentially as per Example 2, the hybridised and biotinylated slides were incubated with 100 µl PLC anti-fluorescein conjugate, washed and incubated with 100 µl liposome avidin-FITC preparation. Slides were washed in a solution of 2×SSC for 5 minutes at room temperature. A second round of amplification was applied by the addition of 100 µl of PLC-antifluorescein conjugate in PBS 5% BSA and incubation as previously. Slides were washed three times in a solution of 2×SSC for 5 minutes each time at room temperature, and further 100 µl liposome avidin-FITC preparation applied. Coverslips were placed over the area of the liposome solution and the slides incubated in the dark for up to 30 minutes. Slides were washed, counterstained and mounted for fluorescence microscopy as previously. Comparison of fluorescent signals after two rounds of amplification compared with a single round of amplification result in an estimated 10-fold enhancement in signal and approximately 100 fold increment in signal over non-amplified signals.

EXAMPLE 4

Fluorescence in situ Hybridisation (FISH) Multiplex Assay

Method of FISH With Two Hybridisation Probes

In a simultaneous assay for chromosome 18 and chromosome 21, an in situ hybridisation probe for chromosome 18 labelled with digoxigenin (Boehringer Mannheim, #1666509 Lewes, UK) and an in situ hybridisation probe for chromosome 21 labelled with fluorescein (Biovation #FPF2110.5x Aberdeen, UK) were used. Hybridisation was carried out to human peripheral blood lymphocytes. Sample preparation, hybridisation conditions and post hybridisation washes were carried out as described for Example 2. Following post-hybridisation washes, slides were further reacted with the biotinylating agent EZ-link Sulfor-NHS-LC-Biotin (Pierce, Chester, U.K.; #21335) as previously described.

Method for Preparation of Unilamellar Liposomes Susceptable to β-Galactosidase Mediated Disruption Unilamellar liposomes (200 nm diameter) were prepared broadly as described for Example 2, with membranes comprising of unsaturated phoshatidylethanolamnine (PE) (Lipid Products, Nutfield UK) stabilised with 5 mole percent of monosialogangliocide GM1 (Sigma, #G7641 Poole, UK). Avidin-rhodamine (Vector Labs #A2012, Peterborough, UK) at a concentration of 0.5 mg/ml was entrappped in PS-GM1 liposomes. Incubation of β-galactosidase (Sigma, #G8023 Poole, UK) at a concentration of 100 ug/ml in 100 mM tris/HCL pH 7.6 at 37° C. with 50 ml PS-GM1/avidin-rhodamine liposomes resulted in a distinct colour change (to pale red), as β-galactosidase mediated de-galatosilation de-stabilised the liposomal membrane allowing release of the avidin-rhodamine into solution.

Method for Conjugation of β-Galactosidase to an Anti-Dioxigenin Antibody

Recombinant β-galactosidase (Sigma, #G8023 Poole, UK) was conjugated at equimolar ratio to an anti-digoxigenin antibody (Boehringer Mannheim #1333062 Lewes, UK), using sulpho-MBS (m-Maleimidobenzoyl-N-hydroxysuccinimide ester) (Pierce,Chester, U.K.; #22312) as cross-linking reagent. Conjugation was performed using the manufacturers recommended protocol. Reagents were desalted and purified post-conjugation using G25 Sephadex columns (Pharmacia, Uppsala Sweden; #17-0851-01), and conjugation verified by SDS polyacrylamide gel electrophroresis and Coomasie Blue staining according to standard protocols (in *Antibodies A Laboratory Manual* eds Harlow E. & Lane D. Cold Spring Harbour Laboratory Press 1988, NY, U.S.A.).

Method for Treatment of Slides With Two Types of Liposome Simultaneously

Slides were treated with conjugated or recombinant phospholipase C anti-fluorescein and at the same time a conjugated β-galactosidase anti-digoxigenin molecule. The phospholipase C anti-fluorescein conjugate binds to the sites of chromosome 21 hybridisation and the β-galactosidase anti-digoxigenin conjugate binds to the site of chromosome 18 hybridisation. Conjugates were added in equimolar ratio in a volume of 100 μl. Slides were washed by incubation in 2×SSC (1×SSC is 0.15M NaCl/0.015M Na Citrate pH7.0) and 100 μl of a 1:1 mixture of liposomes formulated with unsaturated lecithin/cholesterol and containing avidin-FITC and PS-GM1/avidin/rhodamine liposomes was applied to the slides. The liposome mixture was covered with a coverslip and allowed to incubate for a maximum of 30 minutes at 37° C. in the dark. For some experiments incubation was for 10 minutes. Slides were washed and counterstained as previously. Following counterstaining, slides were examined by fluorescence microscopy where an amplified yellow (rhodamine/FITC mix) signal originates from the presence of chromosome 18 in the sample, and an amplified green signal from the presence of chromosome 21 in the sample.

What is claimed is:

1. A method for the amplification and/or creation of a signalling event for detecting a reaction of a probe with a test substance, the method comprising causing the test substance to react with the probe, and identifying reaction of the test substance and the probe by the release of a signalling moiety from within a vesicle, where the signalling moiety reacts and/or binds with a solid or semi-solid phase in the vicinity of the probe.

2. A method as claimed in claim 1, wherein the signalling moiety is in active but ineffective form.

3. A method as claimed in claim 1, wherein the signalling moiety reacts with a receptor on the solid or semi-solid phase.

4. A method as claimed in claim 1, wherein the probe is, or is caused to be, directly or indirectly linked to means for releasing the signalling moiety from the vesicle.

5. A method as claimed in claim 1, wherein the vesicle is a liposome, a red blood cell, any other eukaryotic cell, a prokaryotic cell, a lipase-based emulsion, a lipid-based artificial membrane, or a combination thereof.

6. A method as claimed in claim 1, wherein means to release the signalling moiety is a lipase, a galactosidase, a detergent, animal complement, cytolysin, or a combination of two or more thereof.

7. A method as claimed in claim 1, wherein the signalling moiety comprises a binding molecule, a bacteriophage, a virus, a nucleic acid sequence, an enzyme, or a combination of two or more thereof.

8. A method as claimed in claim 1, wherein the signalling moiety causes signal amplification by release of further signalling moiety from a further vesicle.

9. A kit for the detection of a probe which reacts with a test substance, the kit comprising:

a vesicle which contains a signalling moiety, a probe, means for releasing the signalling moiety from the vesicle, and a solid or semi-solid phase that the signalling moiety can react and/or bind with.

10. A kit as claimed in claim 9, wherein the signalling moiety is in an active but ineffective form.

11. A kit as claimed in any one of claims 9 or 10, wherein the vesicle is a liposome, a red blood cell, any other eukaryotic cell, a prokaryotic cell, a lipase-based emulsion, a lipid based artificial membrane, or a combination of two or more thereof.

12. A kit as claimed in claim 9, wherein the means to release the signalling moiety from the vesicle is a lipase, a galactosidase, a detergent, animal complement, cytolysin, or a combination of two or more thereof.

13. A kit as claimed in claim 9, wherein the signalling moiety comprises a binding molecule, a bacteriophage, a virus, an enzyme, or a combination of two or more thereof.

* * * * *